United States Patent [19]

Daynes et al.

[11] Patent Number: 4,915,109
[45] Date of Patent: Apr. 10, 1990

[54] DEFIBRILLATOR ELECTRODE ADAPTOR

[75] Inventors: John C. Daynes, Redmond; Harry R. Settle, Seattle; Steven A. Chennault, Mukilteo, all of Wash.

[73] Assignee: Physio-Control Corporation, Redmond, Wash.

[21] Appl. No.: 248,794

[22] Filed: Sep. 23, 1988

[51] Int. Cl.⁴ .............................................. A61N 1/00
[52] U.S. Cl. ............................................... 128/419 D
[58] Field of Search ................... 128/419 D, 695, 696, 128/709, 908

[56] References Cited

U.S. PATENT DOCUMENTS 4,610,254 9/1986 Morgan et al. ................. 128/419 D Primary Examiner—Francis Jaworski
Assistant Examiner—George Manuel
Attorney, Agent, or Firm—Christensen, O'Connor, Johnson & Kindness

[57] ABSTRACT

Disclosed is an adaptor (28, 90) for use with a paddle electrode equipped defibrillator (10) that allows alternative use of disposable defibrillation electrodes. In some applications, the adaptor (28, 90) is positioned and retained in the paddle electrode stowage region (18) of the defibrillator (10) with the paddle electrodes (14, 16) being retained in an accessible position by the adaptor. Electrical contacts (75) and a cable (34) that are included in the adaptor electrically connect the paddle electrodes (14, 16) with connectors for disposable defibrillation electrodes, which are mounted at the distal end of the adaptor cable (34). When disposable defibrillation electrodes (36, 38) are placed in the adaptor cable connectors and positioned on the body of a patient, a defibrillation sequence is carried out utilizing the same controls and sequence that are used to defibrillate with the paddle electrodes. In other applications, the adaptor (90) is affixed to a portion of the defibrillator cabinet (92) or another suitable place.

7 Claims, 4 Drawing Sheets

DEFIBRILLATOR ELECTRODE ADAPTOR

FIELD OF THE INVENTION

This invention relates to defibrillators and, more particularly, to means for adapting defibrillators that are equipped with paddle electrodes for selective, alternative use with disposable defibrillator electrodes.

BACKGROUND OF THE INVENTION

Current state-of-the-art defibrillators that are used for emergency resuscitation typically include a pair of hand-held paddle electrodes that are used to transfer a pulse of electrical energy to the body of a patient. As is known in the art, one of the first steps of using the paddle electrodes in an attempted resuscitation (or other therapeutic procedures such as cardioversion) involves coating the surface that will contact the body of the patient with an electrically conductive gel or other material. The paddle electrodes are then placed against the patient's body with the gel serving as a low-impedance interface and the electrodes being positioned so that a pulse of electrical current that passes between the electrodes travels through the patient's heart. Currently, one of two electrode placement arrangements is preferred. In the first arrangement, which is known as anterior/anterior placement, one paddle electrode is placed lateral to the upper sternum and below the right clavicle on the right-hand portion of the patient's chest and the second paddle is placed on the patient's lower left chest, usually below and lateral to the cardiac apex. In the second currently preferred electrode placement, which is known as anterior/posterior placement, one electrode is placed on the patient's chest over the precordium and the second electrode is placed on the patient's back behind the heart.

A patient requiring emergency resuscitation usually is unconscious. Since both hands of the operator must be utilized to hold the paddle electrodes properly and firmly in position and since the defibrillator operator must otherwise remain clear of the patient during the defibrillation procedure, paddle electrodes are not well suited for anterior/posterior use. Even in non-emergency usage such as cardioversion where the patient often is conscious or at least responsive to voice command, it is inconvenient to use paddle electrodes in the anterior/posterior positioning arrangement. Specifically, during such procedures, the patient usually is lying on his or her back to facilitate both the positioning of defibrillator electrodes and conventional ECG electrodes that are utilized in monitoring the patient's cardiac rhythm during the procedure.

Over the past several years, considerable effort has been expended to develop disposable defibrillator electrodes that can be used as an alternative to paddle-type electrodes. This effort has resulted in disposable defibrillation electrodes that exhibit electrical characteristics comparable to paddle electrodes. These disposable defibrillation electrodes are relatively flexible, exhibit a relatively low profile, and include an adhesive peripheral region that allows the electrode to be secured to the patient's skin. Thus, disposable defibrillation electrodes are better suited for anterior/posterior electrode positioning than are paddle-type electrodes. Moreover, disposable defibrillation electrodes sometimes are preferred regardless of whether anterior/anterior or anterior/posterior electrode placement is to be used. For example, it often is desirable to maintain a defibrillator in a ready or standby condition when a patient who has been resuscitated outside a clinical environment is being moved to a hospital or other care facility, during intensive clinical care of a cardiac patient, and during the performance of various medical procedures. In this situations, disposable defibrillation electrodes can be properly positioned and attached to the patient's skin before an emergency arises, thereby facilitating rapid defibrillation should the procedure subsequently be needed.

Since the alternative use of paddle electrodes or disposable defibrillation electrodes is dictated by the situation at hand and by the personal preference of the medical practitioner, attempts have been made to configure or adopt defibrillators for accommodation of both paddle electrodes and disposable defibrillation electrodes. In the simplest arrangement, the defibrillator includes one or more connectors to which the selected type of electrodes can be electrically interconnected with the defibrillator. One disadvantage of this arrangement is that the paddle electrodes may not be connected to the defibrillator when an emergency arises in which the paddle electrodes are needed. In addition, it has become common practice to mount controls and indicators on the paddle electrodes to facilitate both selection of the defibrillation energy level and administration of the defibrillation energy without assistance of a second person and with minimum attention being pad to controls and indicators that are mounted on the defibrillator unit itself. In such arrangements, selectively connecting the desired electrodes to the defibrillator results in the need for placing a second set of controls and indicators in the defibrillator that duplicates those controls and indicators that are located on the paddle electrodes. This requirement not only results in additional device complexity, but also means that medical personnel that are trained in the use of the device must master two separate control procedures.

One prior art proposal that eliminates a portion of the disadvantages associated with selectively connecting the paddle electrodes or disposable defibrillation electrodes to a defibrillator consists of an accessory unit that is temporarily or permanently mounted to the cabinet of the defibrillator. This prior art arrangement includes a cable having one end adapted for electrical interconnection with a pair of disposable defibrillation electrodes. The second end of the cable is electrically connected to conductive plates that are mounted on the upper surface of the accessory unit. When a defibrillator equipped with the accessory unit is to be used with disposable defibrillation electrodes, the electrode snaps (36, 38) are installed to the accessory unit cable and attached to the patient's body at the desired locations. The pulse of defibrillation energy is then administered when the operator places the paddle electrodes on the two conductive plates of the accessor unit and operates the defibrillator controls in the same manner as is utilized when the paddle electrodes are used in contact with the patent's body.

Although the above-mentioned type of accessory unit allows continued availability of the paddle electrodes and does not require separate indicators and controls when disposable defibrillation electrodes are employed, certain other disadvantages and drawbacks are encountered. For example, a defibrillator using such an accessory must include a relatively flat and rigid surface to which the accessory can be mounted for ready access by the handheld paddles without obstructing various defibrillator controls and indicators or obstructing access to the device for service or battery replacement. Further, this type of prior art arrangement for using disposable defibrillation electrodes offers little or no response time improvement relative to conventional use of the paddle electrodes. Specifically, in order to administer a defibrillation pulse, the operator must grasp the handles of the paddle electrodes, remove the electrodes from their stowage position, place the electrodes on the conductive plates of the accessory unit, and then sequence the defibrillator controls to administer the defibrillation pulse.

U.S. Pat. No. 4,628,935, issued to Jones et al. on Dec. 16, 1986, and assigned to the assignee of this invention discloses a defibrillator arrangement which overcomes the above-discussed prior art disadvantages. In that arrangement, an accessory cassette is provided that is adapted for interconnection of the defibrillator with either disposable defibrillation electrodes of the above-discussed type or with internal electrodes of the type used to effect defibrillation during surgical procedures in which the heart is exposed. In the arrangement of Jones et al., the upper surface of the defibrillator includes a slot for receiving a downwardly extending tabular portion of the accessory cassette. Electrically conductive contact regions positioned on the downwardly extending tabular portion of the cassette establish the necessary circuit paths between the defibrillator and cassette. In addition, when the cassette is installed to the defibrillator, nonconductive portions of the downwardly extending tabular region pass into and separate electrical contacts within the defibrillator to appropriately modify the defibrillator electrical circuitry for operation with the cassette.

Although the arrangement disclosed by Jones et al. overcomes the above-discussed disadvantages of the prior art, a need exists for alternative arrangements. For example, the arrangement of Jones et al. is not well suited for retrofit applications in which it is desirable to adapt previously manufactured defibrillators that are equipped only with paddle electrodes for use with disposable defibrillation electrodes. In addition, the arrangement of Jones et al. satisfies a design constraint that is not present in all situations. In particular, the arrangement disclosed by Jones et al. allows the defibrillator to be readily adapted for provision of various features. For example, one commercial embodiment of the arrangement of the Jones et al. patent includes not only a cassette for adapting the defibrillator for use with disposable defibrillation electrodes, but also includes an optional cassette for adapting the device to operation as an external cardiac pacemaker. Numerous design situations arise in which the plug-in feature versatility of the Jones et al. apparatus is not required. It is those situations and the previously mentioned retrofit situations, to which the present invention is directed.

SUMMARY OF THE INVENTION

In accordance with this invention, alternative use of disposable defibrillation electrodes is provided for paddle electrode equipped defibrillators by an adaptor which holds and retains the paddle electrodes in a convenient position for use by the defibrillator operator. In some embodiments of the invention, the adaptor is temporarily or permanently affixed to an available surface region of the defibrillator or even some structure other than the defibrillator. In other embodiments, the adaptor is retained in the portion of the defibrillator that is configured for stowage of the paddle electrodes. More specifically, a common defibrillator design objective is stowage of the paddle electrodes in a manner that positions the electrodes for rapid access and simultaneously retains the paddle electrodes so they will not be physically displaced until they are intentionally withdrawn by the defibrillator operator. Although there is some variation in the location of the paddle electrode stowage region, the electrodes often are stowed in a shallow well or shelf-like region of the defibrillator with the handles of the paddle electrodes facing upwardly for easy and rapid access. Various arrangements can be used for retaining the paddle electrodes in the stowed position with the primary design factor often being the intended use of the defibrillator. For example, a defibrillator that is designed for use primarily by field resuscitation teams such as paramedics must retain the stowed paddle electrodes under far more rigorous transportation conditions than a defibrillator that is designed primarily for use in a hospital operating room or even a defibrillator that is designed for inclusion in a cardiac crash cart.

Regardless of the exact arrangement utilized for retainment of the paddle electrodes in the stowed condition in those embodiments of this invention that are retained within the paddle electrode stowage region, the adaptors are configured for easy insertion into the defibrillator paddle electrode stowage region with portions of the adaptor base that interact with the paddle electrode stowage provisions of the defibrillator being configured and contoured to match corresponding portion of the paddle electrodes.

In all embodiments of the invention, the paddle electrodes are placed in electrode retainment provisions of the adaptor which position the electrodes so that the electrode handles can easily be grasped by an operator. Mounted within the adaptor and adjacent the skin-contacting portion of each paddle electrode is a set of one or more adaptor contacts for electrically interconnecting each of the paddle electrodes to the adaptor. A two-conductor cable having one end configured for connection with a pair of disposable defibrillator electrodes is electrically connected to the adaptor contact sets. Thus, when the defibrillation controls of paddle electrodes that are stowed in the adaptor of the invention are activated to supply a pulse of defibrillation current, the current passes through one set of the adaptor contacts; through one conductor of the adaptor cable; is coupled through the patient by means of the disposable defibrillation electrodes; and returns to the second paddle electrode by means of the second conductor of the adaptor cable and the second set of adaptor contacts.

BRIEF DESCRIPTION OF THE DRAWINGS

The various features and advantages of the invention will be better understood with reference to the following description and the accompanying drawings in which.

DETAILED DESCRIPTION

Figure 1:
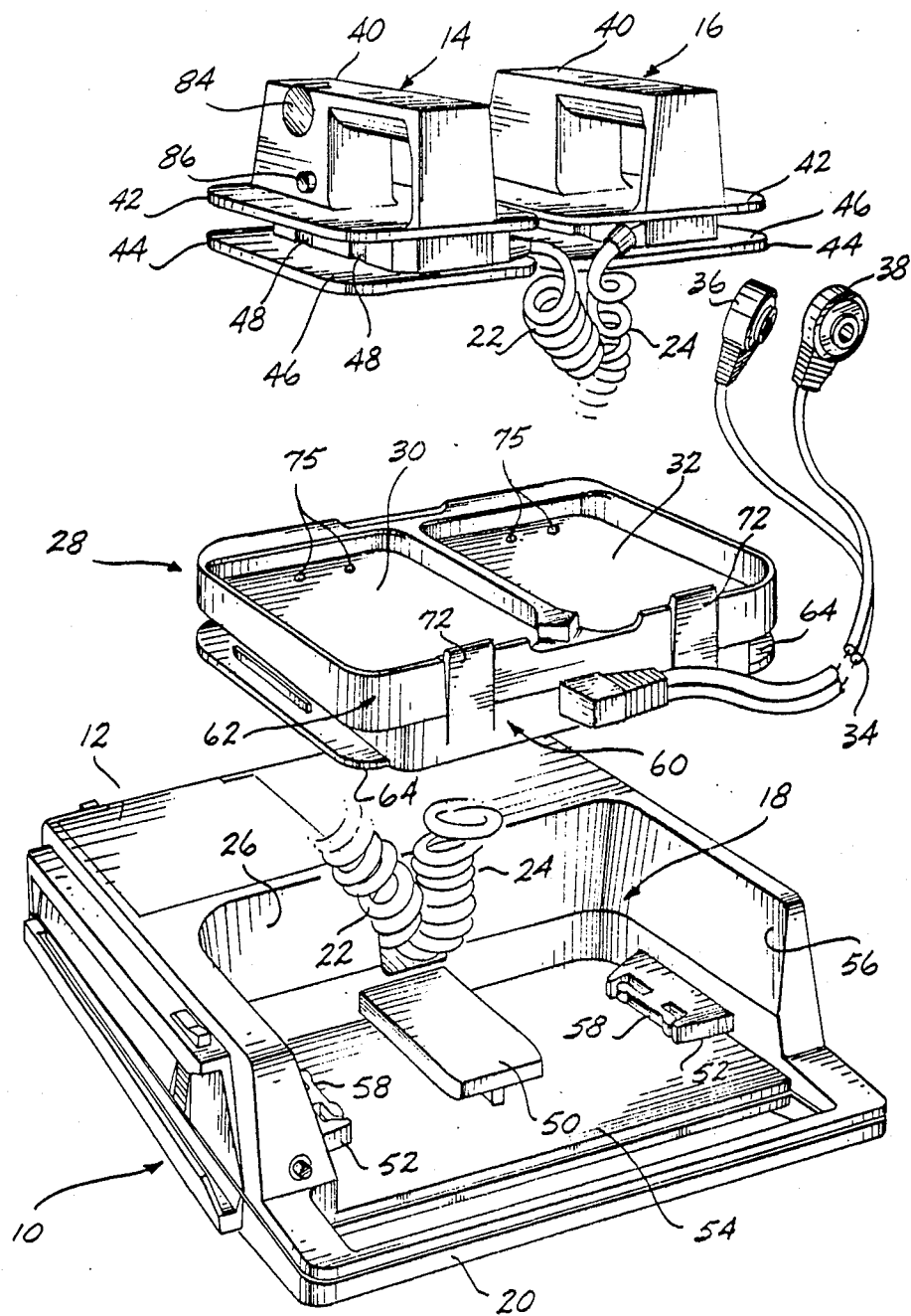
FIG. 1 is an exploded isometric view that illustrates a paddle electrode equipped defibrillator and an embodiment of the electrode adaptor of this invention.

Illustrated in FIG. 1 a defibrillator 10 that includes a housing unit 12 and a pair of paddle electrodes 14 and 16. Formed in housing 12 is a three-sided, recessed electrode stowage region 18 that is located immediately behind a forwardly extending carrying handle 20. Paddle electrodes 14 and 16 are electrically connected to defibrillation pulse forming and control circuity (located within defibrillator 10 and not shown in FIG. 1) by cables 22 and 24, respectively, which pass through an opening in the central region of an upwardly extending end wall 26 of recess 18 that is substantially parallel to carrying handle 20.

Shown also in FIG. 1 is a paddle adaptor 28 which is configured for insertion in electrode stowage region 18 of defibrillator 10 with paddle electrodes 14 and 16 then being retained and stowed in relatively shallow paddle stowage wells 30 and 32, respectively, which are formed in the upper surface of paddle adaptor 28. Extending from paddle adaptor 28 is a two-conductor cable 34 having an electrode connector 36, 38 installed at the distal end of each cable conductor. Electrode connectors 36 and 38 are configured for mechanical and electrical interconnection with a pair of disposable defibrillator electrodes (not shown in FIG. 1). As will be described in more detail in the following paragraphs, when paddle adaptor 28 is installed in stowage recess 18 of defibrillator 10 and the paddle electrodes 14 and 16 are placed in electrode wells 30 and 32 of paddle adaptor 28, an electrical signal path is established between one of the electrode connectors 36 or 38 and the electrically conductive region of paddle electrode 14 that normally is utilized to couple a defibrillation pulse to the patient. Similarly, an electrical signal path is established between the second electrode connector 36 or 38 and the electrically conductive portion of paddle electrode 16 that normally couples the defibrillation pulse to the patient. Thus, when electrode connectors 36 and 38 are attached to disposable defibrillation electrodes that are properly positioned on a patient, the defibrillator controls can be sequenced in the normal fashion to execute a defibrillation procedure that uses the disposable defibrillation electrodes in place of the paddle electrodes.

Figure 2:
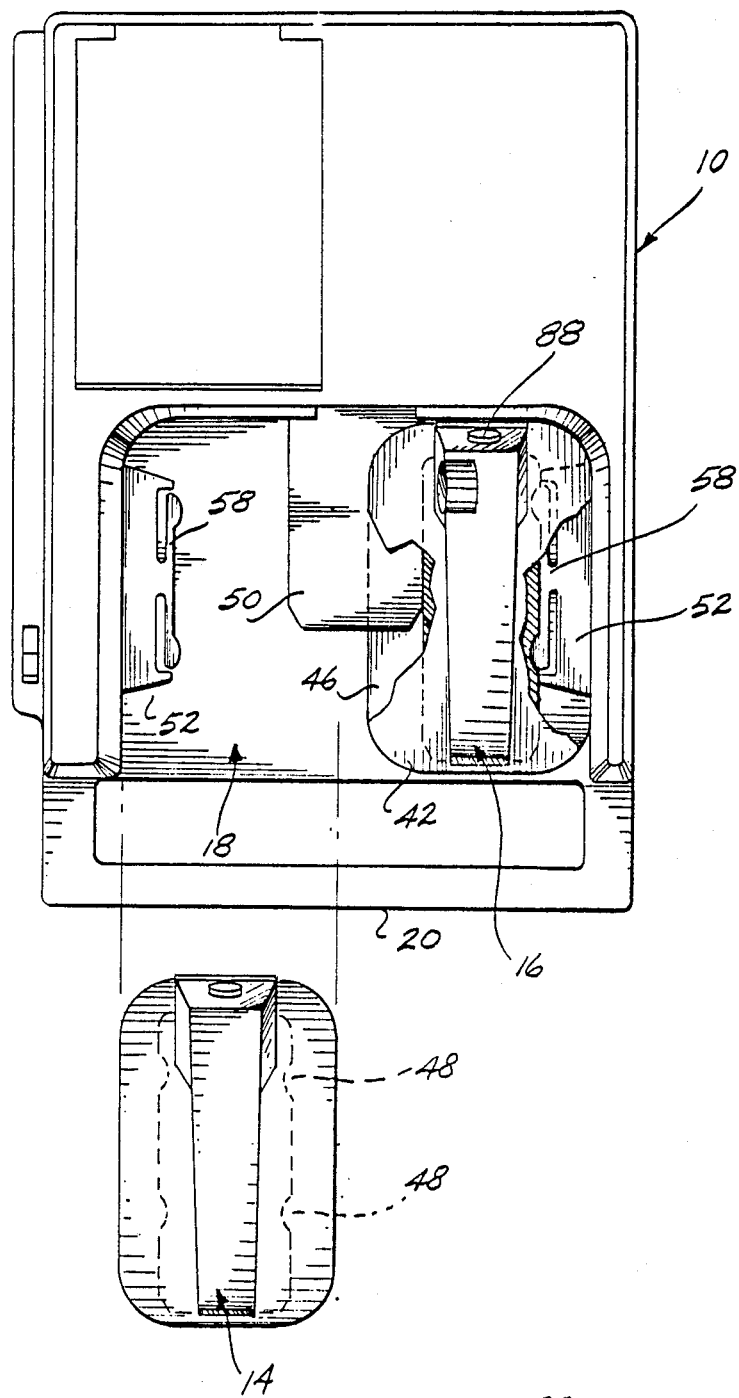
FIG. 2 is a top view that illustrates the paddle electrode stowage provisions of the defibrillator shown in FIG. 1.
Figure 3:
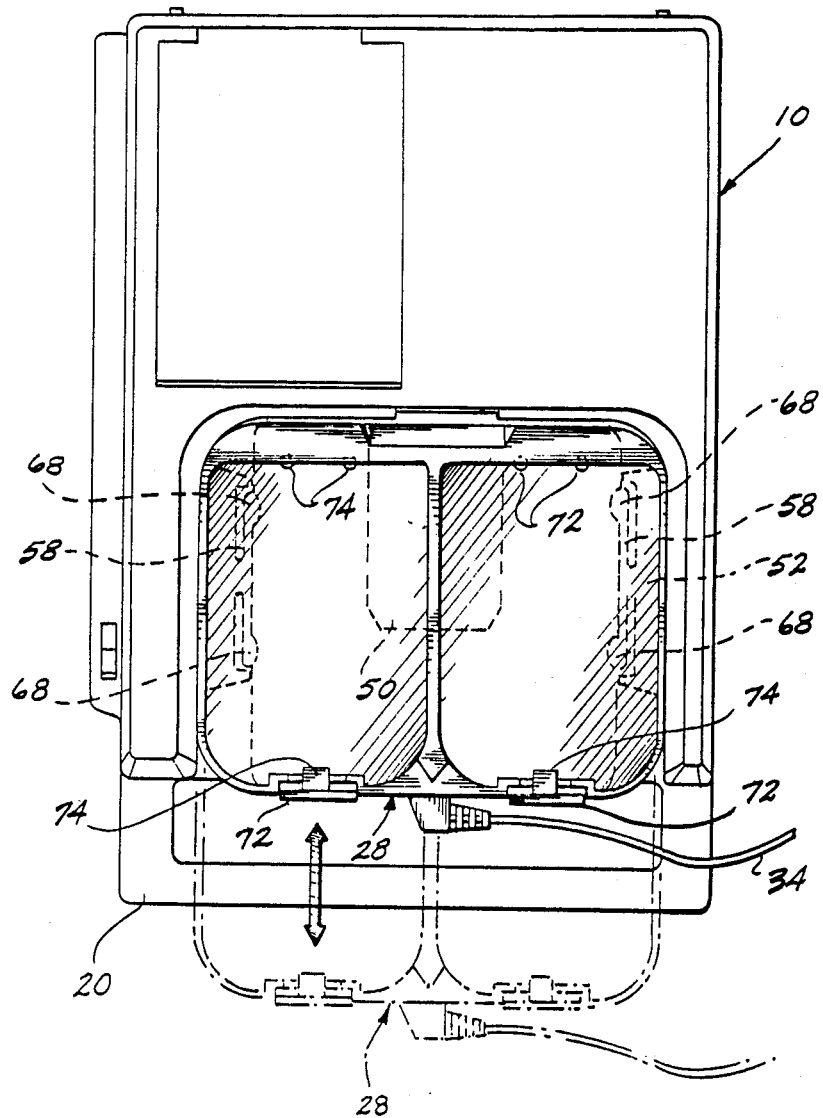
FIG. 3 is a partially cutaway top view illustrating the adaptor of FIG. 1 installed in the defibrillator.

FIGS. 2 and 3 are top views of defibrillator 10 which respectively illustrate the stowage of paddle electrodes 14 and 16 in stowage region 18 (paddle adaptor 28 not being utilized) and the manner in which paddle adaptor 28 is retained in stowage region 18 of defibrillator 10 (paddle adaptor 28 being utilized). As can be seen in both FIG. 1 and FIG. 2, the lower portion of paddle electrodes 14 and 16 each include an upwardly extending body portion 40 that is somewhat U-shaped in geometry to form handles that can easily be grapsed by the defibrillator operator. Located below body portion 40 of each paddle electrode is an upper plate 42 of substantially rectangular geometry that extends outwardly from body portion 40. Spaced apart and from and substantially parallel to each upper plate 42 is a lower plate 44 of size and geometry substantially identical to upper plate 42. In this arrangement, the lower surface of lower plate 44 includes the electrically conductive electrode region that is coated with a conductive gel and pressed against the patient's body when paddle electrodes 14 and 16 are utilized in a resusctation attempt (electrode plate 80 in FIG. 4). Upper plate 42 provides a nonconducting barrier that aids in insuring that the operator will not come into contact with the electrodes and, in conjunction with spaced-apart lower plate 44, forms a groove 46 that extends around the lower periphery of each paddle electrode 14 and 16. Use of groove 46 to separate the outer edge region of upper plate 42 from lower plate 44 establishes a relatively long current path that must be transverse before the defibrillator operator can become the inadvertent recipient of electrical energy that is intended for the patient. In addition, in the depicted defibrillator arrangement groove 46 is utilized in retaining the paddle electrodes 14 and 16 in electrode stowage region 18. Two spaced-apart arcuate retainer grooves 48 are included in each of the lateral walls that extend between upper and lower plates 42 and 44 to form the inner boundary of groove 46.

With continued reference to FIGS. 1 and 2, when paddle electrodes 14 and 16 are stowed in stowage region 18 of defibrillator 10, the paddle electrodes are retained by a T-bar 50 and two side retaining guides 52. As is shown in FIG. 1, T-bar 50 includes a transverse leg that extends substantially parallel to bottom wall 54 of stowage region 18 and a vertical leg that is joined to or formed in bottom wall 54. In addition, T-bar 50 is positioned and dimensioned so that the paddle electrodes 14 and 16 can be slid into stowage region 18 with the electrode plate 80 of the paddle electrode resting on bottom wall 54 of stowage region 18 and the transverse leg of T-bar 50 projecting into groove 46 of the paddle electrode.

The side retaining guides 52 are mounted on or formed in the oppositely disposed sidewalls 56 of stowage region 18, with each side retaining guide 52 being dimensioned and positioned so that it projects into groove 46 when the paddle electrodes 14 and 16 are slid into the stowage position (FIG. 2). When viewed from the top, side retaining guides 52 are of trapezoidal geometry, having a recessed central region that includes a T-shaped paddle retainer 58. Located along each of the outward ends of the T-shaped paddle retainer 58 is a semicircular projection that is received by a paddle electrode arcuate retainer groove 48 when paddle electrodes 14 and 16 are slid into the stowed position.

It can be noted that T-bar 50 and side retaining guides 52 interact with paddle electrodes 14 and 16 to retain the paddle electrodes firmly in stowage region 18 with the handle-like body portions extending upwardly for easy access by the defibrillator operator. Although paddle electrodes 14 and 16 are firmly retained when stowed, the paddle electrodes may be easily withdrawn and applied to a patient.

Figure 4:
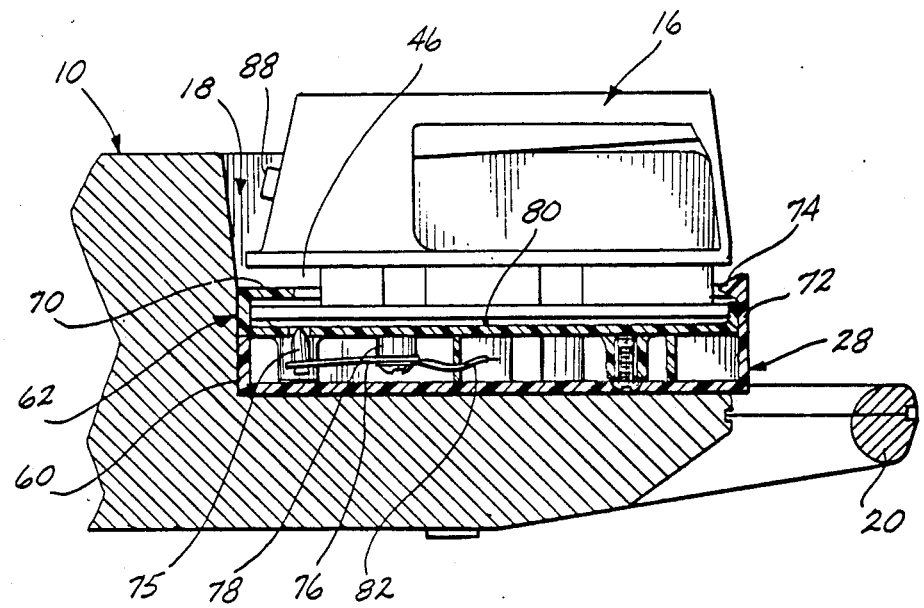
FIG. 4 is a side elevation view of the adaptor of FIG. 1.

The manner in which paddle adaptor 28 of this invention is configured for insertion in paddle electrode stowage region 18 of defibrillator 10 can be understood that reference to FIG. 1 and FIGS. 3 and 4. As is best seen in FIG. 1, the depicted embodiment of adaptor 28 includes joined-together lower and upper adaptor housing units 60 and 62, respectively. Lower adaptor housing unit 60 includes flanges 64 that extend outwardly from the lateral, oppositely disposed sidewalls of lower housing units 60. Upper housing unit 62 is substantially rectangular in geometry and includes upwardly extending wall regions that define paddle electrode stowage wells 30 and 32. As is shown in FIG. 1, the oppositely disposed lateral side regions of upper adaptor housing unit 62 project outwardly over flanges 64 of lower housing unit 60. This forms laterally extending slots 66 that receive side retaining guides 52 when paddle adaptor 28 is slid into paddle electrode stowage region 18 of defibrillator 10. As can be seen in FIG. 3, when adaptor 28 is slid into position within electrode stowage region 18, the outwardly projecting end regions of the T-shaped paddle retainers 58 are received in arcuate grooves 68 that extend upwardly along the side walls of lower adaptor housing unit 60.

In the currently preferred realizations of the embodiment depicted in FIGS. 1-4, adaptor 28 does not engage with T-bar 50 of electrode stowage region 18. Specifically, lower adaptor housing unit 60 includes an upwardly extending well region that allows adaptor 28 to pass into electrode stowage region 18 without interference or engagement with T-bar 50.

Upper adaptor housing unit 62 is specifically arranged for storage of paddle electrodes 14 and 16 in a position that allows the defibrillator operator to easily grasp the paddle electrodes and withdraw them for use in the conventional manner, or, in the alternative, to utilize the electrodes in the stowed position to sequence and control the defibrillation procedure utilizing disposable defibrillation electrodes that are secured to connectors 36 and 38 of adaptor cable 34. Specifically, the forward end of upper adaptor housing 62 includes a flange 70 that extends rearwardly and is spaced apart from the lower surface of paddle stowage wells 30 and 32. As can best be seen in FIG. 4, when paddle electrodes 14 and 16 are retained by adaptor 28, flange 70 extends into the portion of grooe 46 that is located along the forward end of the paddle electrode.

With primary reference to FIGS. 1, 3 and 4, the rearward end of paddle electrodes 14 and 16 are retained in paddle electrode stowage wells 30 and 32 by upwardly extending retainers 72 that are formed in lower adaptor housing unit 60. As is best shown in FIG. 1, retainers 72 are substantially rectangular and extend upwardly passing adjacent to the recesses in the wall of upper housing unit 62. Located along the forward edge of each retainer 72 is an outwardly projecting region 74 that is received in groove 46 of paddle electrodes 14 and 16. Relatively thin slots extend downwardly along the sides of retainer 72 into the wall of lower housing unit 60 to allow the upper end of the retainers 72 to swing slightly rearward so that the retainers disengage paddle groove 46 when the paddle electrodes are inserted into or withdrawn from paddle electrode stowage wells 30 and 32.

In the depicted embodiment of paddle adaptor 28, the paddle electrodes are electrically connected to adaptor 28 by means of two adaptor contacts 75 that are located in each of the electrode stowage wells 30 and 32. As is best seen in FIG. 4, each adaptor contact 75 is mounted at the end of an electrically conductive spring strip 76 that extends from a downwardly extending mounting boss 78 that is formed on the lower surface of upper adaptor housing unit 62. Spring strip 76 urges the associated pair of adaptor contacts 75 upwardly to insure good electrical contact with the electrode plates 80 of paddle electrodes 14 and 16. Extending from mounting boss 78 and in electrical contact with spring strip 76 is a wire 82 that connects the adaptor contact 75 of paddle electrode stowage wells 30 and 32 to the two separate conductors of adaptor cable 34.

When adaptor 28 is installed in paddle electrode stowage region 18 of defibrillator 10, a defibrillation procedure utilizing disposable defibrillation electrodes is effected in the following manner. With paddle electrodes 14 and 16 stowed in paddle electrode stowage wells 30 and 32, disposal electrodes are installed to connectors 36 and 38 of adaptor cable 34 and the electrodes are appropriately placed on the patient's body. An energy selector switch (84 in FIG. 1) is then operated to set the defibrillation energy to be supplied to the patient. A control the causes the defibrillator to charge to the selected energy level is then activated (typically a push-button switch located on one of the paddle electrodes 14 and 16; not shown in the figures). When the defibrillator 10 is charged, a defibrillator "ready" indicator is energized, e.g., indicator 86 of paddle electrode 14 (FIG. 1). Once the system is ready to supply the selected pulse of defibrillation energy, the operator simultaneously depressed discharge switches 88 (FIG. 2) which are located in the handle region of paddle electrodes 14 and 16. This causes electrical energy supplied by defibrillator 10 to flow through the patient's heart by means of a circuit path which paddle adaptor 28 establishes between paddle electrodes 14 and 16. Specifically, and as described above, electrical current flows from electrode plate 80 of one of the paddle electrodes 14 or 16 through the contacting adaptor contacts 75, the associated spring strip 76, wire 82 and the conductors of adaptor cable 34.

In view of the above description, it can be noted that defibrillator 10 in adaptor 28 can be repeatedly operated to supply a sequence of defibrillation pulses to a set of disposable defibrillation electrodes if such repeated defibrillation attempts must be made. Further, should the operator wish to apply the defibrillation pulses via the paddle electrodes instead of via disposable defibrillation electrodes, the operator need only withdraw the electrodes, prepare the skin-contacting portion of the electrodes in the normal manner and perform the defibrillation sequence in the normal way. Likewise, in situations in which a patient initially has been defibrillated with the paddle electrodes, and it is either desired or necessary to maintain the defibrillator on a standby basis, disposable defibrillation electrodes can be installed and the paddle electrodes placed in adaptor 28.

Certain commercially available defibrillators include test loads that are electrically interconnected with contacts that are positioned in the paddle electrode stowage region so that the paddle electrode plates are electrically connected to the test loads when the paddles are stowed. In these arrangements, the defibrillator can be discharged into the test loads when the operator wishes to verify proper operation. If adaptor 28 is installed in the stowage region 18 of such a defibrillator, procedures must be adopted to insure that a test procedure in which the defibrillator is normally discharged into the test loads does not take place. Specifically, should the adaptor be interconnected with disposable defibrillation electrodes that are placed on a patient, the patient will receive an unintended defibrillation pulse. Even if the adaptor is not connected to disposable defibrillation electrodes that are positioned on a patient, a high electrical potential will be generated between the electrode connectors (or disposable defibrillation electrodes installed thereto). This potential may result in current flow between the electrode connectors (or one connector and surrounding structure) or can result in damage to the defibrillator circuitry.

Figure 5:
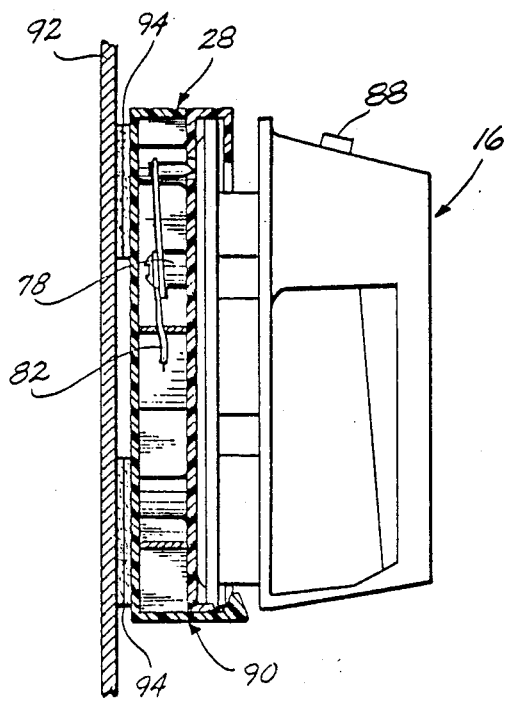
FIG. 5 is a side elevation view which illustrates the invention embodied for temporary attachment either to a portion of the defibrillator other than the paddle electrode stowage region, or to structures other than the defibrillator.

As an accommodation in defibrillators that use the above-described type of test loads, the adaptor of this invention can be temporarily attached to a portion of the defibrillator or other nearby structure. For example, FIG. 5 illustrates a paddle adaptor 90 that is temporarily affixed to an available region of the defibrillator housing 92 (e.g., a side panel of the defibrillator). Various means can be used to hold paddle adaptor 90 in the desired position. In the arrangement of FIG. 5, strips 94 of hook and pile fabric material of the type sold under the trademark VELCRO are used, with one portion of the material being bonded by conventional adhesive to housing 92 and the other portion being bonded to the lower face of paddle adaptor 90.

Although FIG. 5 illustrates a paddle adaptor 90 that is identical to paddle adaptor 28 of FIGS. 1-4 (except for strips 94), it will be recognized that such an embodiment of the invention need not include the previously-discussed structural features that retain adaptor 28 in electrode stowage region 18 of defibrillator 10. In it fact will be recognized by those skilled in the art that the above-discussed embodiments of the invention are exemplary in nature. Specifically, in the broadest sense, the practice of the invention requires only that paddle adaptors be mountable for ready access by the defibrillator operator with the paddle electrodes being retained in the paddle electrode without being held in place by the operator. According to another aspect of the invention, the paddle can be configured for insertion in the electrode stowage region of the defibrillator with which the adaptor is used. Although currently available defibrillators and newly designed defibrillators vary somewhat in the arrangement for paddle electrode stowage, the invention can be arranged to mechanically interface with (and preferably to be retained by) the same defibrillator structure that provides for stowage of the paddle electrodes. For example, in one realization of the invention that is currently being developed, the adaptor is configured for retainment by depressable latches that are located in the floor of the electrode stowage region. In this same realization, the adaptor does not include a flange 70 (FIG. 4) for retainment of the forward end of the paddle electrodes, since a comparable structure is included in the defibrillator.

The embodiments of the invention in which an exclusive property or privilege is claimed are defined as follows:

1. An adaptor for use with a defibrillator of the type that includes a pair of paddle electrodes, said adaptor for converting the defibrillator for alternative use of the defibrillator with a pair of disposable electrodes other than the paddle electrodes, said adaptor comprising:
   an adaptor body, said adaptor body including means for receiving and retaining in a predetermined position the paddle electrodes of the defibrillator;
   first and second adaptor contact means, said first adaptor contact means being mounted to provide electrical contact with the first one of the pair of paddle electrodes when that paddle electrode is received and retained by said adaptor body, said second adaptor contact means being mounted to provide electrical contact with the second one of the pair of paddle electrodes when that paddle electrode is received and retained by said adaptor body; and
   conductor means for electrically connecting said first adaptor contact means to a first of said disposable electrodes and for electrically connecting said second adaptor contact means to a second of said disposable electrodes.

2. The adaptor of claim 1 wherein said defibrillator further is of the type that includes a region for stowage of the pair of paddle electrodes and wherein said adaptor body is adaptor for placement in said region for stowage when the paddle electrodes are received and retained.

3. The adaptor of claim 2 wherein the electrode stowage region of the defibrillator includes retainment means for retaining the paddle electrodes in a stowed condition and said adaptor body further includes means for engaging the retainment means of the electrode stowage region.

4. An adaptor for use with a paddle electrode equipped defibrillator of the type that includes a stowage facility for the paddle electrodes, said adaptor for converting the defibrillator for alternative use with disposable defibrillation electrodes, said adaptor comprising:
   an adaptor body dimensioned and configured for placement in the stowage facility of the defibrillator, said adaptor body including means for receiving the paddle electrodes of the defibrillator;
   first and second adaptor contact means, said first adaptor contact means being mounted to provide electrical contact with the first one of the paddle electrodes when that paddle electrode is received by said adaptor body, said second adaptor contact means being mounted to provide electrical contact with the second one of the paddle electrodes when that paddle electrode is received by said adaptor body; and
   conductor means for electrically connecting said first adaptor contact means to a first of said disposable electrodes and for electrically connecting said second adaptor contact means to a second of said disposable electrodes.

5. The adaptor of claim 4 wherein said means for receiving the paddle electrodes includes means for retaining the paddle electrodes in a predetermined position.

6. The adaptor of claim 5 wherein the electrode stowage facility of the defibrillator includes means for retaining the paddle electrodes in a stowed condition and said adaptor body further includes means for retainment by the retainment means of the electrode stowage facility.

7. In a paddle electrode equipped defibrillator of the type including a stowage region for the paddle electrode and means for temporary retainment of the paddle electrodes in the stowage region, the improvement comprising an adaptor that facilitates alternative use of said defibrillator with a pair of electrodes other than said paddle electrodes, said adaptor being dimensioned and configured for placement in said stowage region and for temporary retainment by said means for temporary retainment of said paddle electrodes, said adaptor including means for temporary retainment of said paddle electrodes, said adaptor further including means for completing a first electrical circuit path between a first one of said other electrodes and a first one of said paddle electrodes when said first paddle electrode is temporarily retained by said adaptor and means for completing a second electrical circuit path between a second one of said other electrodes and a second one of said paddle electrodes.

* * * * *

UNITED STATES PATENT AND TRADEMARK OFFICE
CERTIFICATE OF CORRECTION

PATENT NO. : 4,915,109
DATED : April 10, 1990
INVENTOR(S) : J. C. Daynes et al.

It is certified that error appears in the above-identified patent and that said Letters Patent is hereby corrected as shown below:

| | | |
|---|---|---|
| Column 2 | Line 57 | "accessor" should be --accessory-- |
| Column 5 | Line 10 | after "FIG. 1" insert --is-- |
| Column 5 | Line 16 | "circuity" should be --circuitry-- |
| Column 5 | Line 62 | "grapsed" should be --grasped-- |
| Column 5 | Line 66 | after "apart" delete "and" |
| Column 6 | Line 5 | "resusctation" should be --resuscitation-- |
| Column 6 | Line 26 | after "electrodes are" insert --positioned and-- |
| Column 7 | Line 22 | "storage" should be --stowage-- |
| Column 7 | Line 35 | "grooe 46" should be --groove 46-- |
| Column 8 | Line 19 | "depressed" should be --depresses-- |
| Column 9 | Line 20 | "In it fact" should be --It in fact-- |
| Column 10 (Claim 2, | Line 6 Line 4) | "adaptor" should be --adapted-- |

UNITED STATES PATENT AND TRADEMARK OFFICE
CERTIFICATE OF CORRECTION

PATENT NO. : 4,915,109

DATED : April 10, 1990

INVENTOR(S) : J. C. Daynes et al.

It is certified that error appears in the above-identified patent and that said Letters Patent is hereby corrected as shown below:

Section [56] Additional References after "4,610,254 9/1986 Morgan et al. ......... 128/419 D" insert --4,419,998 12/1983 Heath ......... 128/639
4,494,552 1/1985 Heath ......... 128/696
4,628,935 12/1986 Jones et al. ......... 128/419 D
Des. 244,154 4/1977 Smith et al. ......... 128/419 D--

Signed and Sealed this

Nineteenth Day of January, 1993

Attest:

DOUGLAS B. COMER

Attesting Officer

Acting Commissioner of Patents and Trademarks